(12) United States Patent
Hamatani et al.

(10) Patent No.: US 9,002,687 B2
(45) Date of Patent: Apr. 7, 2015

(54) DEVICE FOR PREDICTING DEFORMATION BEHAVIOR OF RUBBER MATERIAL AND METHOD FOR PREDICTING DEFORMATION BEHAVIOR OF RUBBER MATERIAL

(75) Inventors: Satoshi Hamatani, Higashimurayama (JP); Keizo Akutagawa, Kodaira (JP); Hiroshi Shima, Koganei (JP)

(73) Assignee: Bridgestone Corporation, Tokyo (JP)

( * ) Notice: Subject to any disclaimer, the term of this patent is extended or adjusted under 35 U.S.C. 154(b) by 225 days.

(21) Appl. No.: 13/147,493

(22) PCT Filed: Feb. 2, 2010

(86) PCT No.: PCT/JP2010/051733
§ 371 (c)(1),
(2), (4) Date: Aug. 2, 2011

(87) PCT Pub. No.: WO2010/090295
PCT Pub. Date: Aug. 12, 2010

(65) Prior Publication Data
US 2011/0288838 A1  Nov. 24, 2011

(30) Foreign Application Priority Data
Feb. 3, 2009 (JP) ................................. 2009-022923

(51) Int. Cl.
*G06G 7/48* (2006.01)
*G06F 17/50* (2006.01)
(Continued)

(52) U.S. Cl.
CPC .............. *G01N 3/00* (2013.01); *G06F 17/5018* (2013.01); *G01N 2203/0216* (2013.01); *G06F 2217/80* (2013.01)

(58) Field of Classification Search
USPC ..................................... 703/6, 1, 2
See application file for complete search history.

(56) References Cited

U.S. PATENT DOCUMENTS 6,199,026 B1 * 3/2001 Shiraishi et al. .............. 702/140
(Continued)

FOREIGN PATENT DOCUMENTS

JP          2005-345413        *  6/2004
(Continued)

OTHER PUBLICATIONS

Dommelen et al., A numerical investigation of the potential of rubber and mineral particles for toughening of semicrystalline polymers, Jun. 2003, Computational Materials Science, vol. 27, Issue 4, pp. 480-492.*
(Continued)

*Primary Examiner* — Kamini S Shah
*Assistant Examiner* — Juan Ochoa
(74) *Attorney, Agent, or Firm* — Sughrue Mion, PLLC (57) ABSTRACT

The present invention relates to a method for predicting a deformation behavior of a rubber material capable of accurately analyzing a deformation behavior of a rubber material even in a micro level, and more specifically, to a method for predicting a deformation behavior of a rubber material, including: generating a three-dimensional model of the rubber material formed by adding a filler to a rubber; applying a configuration condition specifying a relationship between a stress and a strain on the basis of thickness information and temperature information obtained on the basis of a molecular dynamics approach to a rubber layer portion constituting the three-dimensional model; and, analyzing the deformation behavior of the rubber material. Further, in the method for predicting a deformation behavior of a rubber material, it is preferable that the deformation behavior of the rubber material is analyzed by applying a finite element method to the three-dimensional model to which the configuration condition is applied.

4 Claims, 7 Drawing Sheets
(2 of 7 Drawing Sheet(s) Filed in Color)

(51) Int. Cl.
*G06F 7/60* (2006.01)
*G01N 3/00* (2006.01)

(56) References Cited

U.S. PATENT DOCUMENTS

| | | | |
|---|---|---|---|
| 7,149,670 B2* | 12/2006 | Iwasaki et al. | 703/8 |
| 7,292,966 B2* | 11/2007 | Naito | 703/6 |
| 7,415,398 B2* | 8/2008 | Naito et al. | 703/6 |
| 7,672,821 B2* | 3/2010 | Hori et al. | 703/6 |
| 2005/0256686 A1* | 11/2005 | Stabelfeldt et al. | 703/6 |
| 2010/0169062 A1* | 7/2010 | Linn et al. | 703/2 |

FOREIGN PATENT DOCUMENTS

| | | | |
|---|---|---|---|
| JP | 2006-200937 | * | 1/2005 |
| JP | 2005-345413 A | | 12/2005 |
| JP | 2006-193560 A | | 7/2006 |
| JP | 2006-200937 A | | 8/2006 |
| JP | 2006-200938 A | | 8/2006 |
| JP | 2007-107968 A | | 4/2007 |
| JP | 2007-272416 A | | 10/2007 |
| JP | 2008-122154 A | | 5/2008 |
| JP | 2008-213724 A | | 9/2008 |

OTHER PUBLICATIONS

Bergstrom et al., Large Strain Time-Dependent Behavior of Filled Elastomers, Nov. 2000, Large Strain Time-Dependent Behavior of Filled Elastomers, Mechanics of Materials, vol. 32, Issue 11, pp. 627-644.*
Bergstrom et al., Mechanical Behavior of Particle Filled Elastomers, 1999, Rubber Chemistry and Technology, vol. 72, No. 4, pp. 1-36.*
Chinese Office Action dated Aug. 23, 2012 issued in Chinese Application No. 201080006555.7.
Korean Office Action dated Oct. 29, 2012 issued in Korean Patent Application No. 10-2011-7018076.
International Search Report for PCT/JP2010/051733 dated May 11, 2010.
Japanese Office Action for JP 2009-022923 dated Apr. 27, 2010.
Chinese Office Action, dated Mar. 21, 2013, issued in corresponding Chinese Application No. 201080006555.7.

* cited by examiner

DEVICE FOR PREDICTING DEFORMATION BEHAVIOR OF RUBBER MATERIAL AND METHOD FOR PREDICTING DEFORMATION BEHAVIOR OF RUBBER MATERIAL

CROSS REFERENCE TO RELATED APPLICATIONS

This application is a National Stage of International Application No. PCT/JP2010/051733 filed on Feb. 2, 2010, which claims priority from Japanese Patent Application No. 2009-022923, filed on Feb. 3, 2009, the contents of all of which are incorporated herein by reference in their entirety.

TECHNICAL FIELD

The present invention relates to a device for predicting a deformation behavior of a rubber material formed by adding a filler such as a carbon black and a silica to a rubber, and a method for predicting a deformation behavior of the rubber material, and in particular, to a method for predicting a deformation behavior capable of precisely analyzing the deformation behavior of the rubber material even in a micro level.

RELATED ART

It has been known that a reinforcing effect can be obtained by adding a filler such as a carbon black and a silica to a rubber, and a rubber material formed by adding the filler to the rubber is used in rubber products such as tires for vehicles. For such a rubber material, deformation behaviors at the time when forces are applied thereto are measured through experiments, and the measurement results are evaluated for designing the amount of the filler contained in the rubber material.

Recently, with development of numerical analysis methods such as a finite element method (FEM) and environments concerning calculators, various methods have been proposed to analyze the deformation behavior by creating a three-dimensional model at a filler portion and a rubber portion in the rubber material. Further, as a method capable of precisely analyzing the deformation behavior of the rubber material while reducing the time required for the analysis, there is a method of capturing an image of arrangement of the filler in the actual rubber material with a transmission electron microscope (TEM); re-structuring the thus obtained data to be a three-dimensional base model through a computed tomography method (CT method); and, predicting the deformation behavior of the rubber material through the finite element method (FEM) (see Japanese Patent Application Laid-open No. 2006-200937 (Patent Document 1)).

Incidentally, as the simplest model for calculation through the FEM in the case where the rubber material contains the rubber and the filler, there is a known method of applying mechanical properties obtained through measurement of the rubber and the filler separately to the three-dimensional model.

However, it is said that polymers existing around the filler are adsorbed with the filler, and have mechanical properties different from those obtained from a polymer itself, and with recent advancement of measurement technique, such a phenomenon has already been confirmed. For example, by measuring an elastic modulus with an atomic force microscope (AFM), it can be known that the polymers existing around the filler have a larger elastic modulus as compared with that in the polymer itself.

RELATED ART DOCUMENT

Patent Document

Patent Document 1: Japanese Patent Application Laid-open No. 2006-200937

DISCLOSURE OF THE INVENTION

Problems to be Solved by the Invention

Therefore, in order to improve analysis accuracy of the deformation behavior of the rubber material, it is necessary to apply a constant, which is different from a material constant obtained from the single rubber, to the rubber portion existing around the filler, namely, a rubber layer portion adsorbed with the filler.

However, in a material exhibiting a non-linearity such as a rubber, it is difficult to apply an appropriate material constant to the rubber layer portion adsorbed with the filler. Further, although the elastic modulus and viscoelasticity of the rubber layer portion adsorbed with the filler can be measured by using the AFM, it becomes difficult to measure them if the amount of deformation of the rubber material increases.

Further, although it may be possible to use a method of modeling the filler and the rubber through a molecular dynamics approach and deforming it to obtain the mechanical properties, the measurable time scale with the molecular dynamics approach is several nanoseconds. According to a temperature-time conversion law concerning a viscoelastic property of polymeric materials, this corresponds to a viscoelastic property in the range of extremely low temperatures, and thus, it is difficult to accurately obtain the mechanical properties.

As described above, problems still exist in accurately analyzing the deformation behavior of the rubber material including the rubber layer portion adsorbed with the filler.

In view of the facts described above, an object of the present invention is to solve the problems of the conventional arts described above, and to provide a method for predicting a deformation behavior of a rubber material capable of accurately analyzing the deformation behavior of the rubber material even in a micro level. Further, another object of the present invention is to provide a device for predicting the deformation behavior of the rubber material to which the method described above can be applied.

Means for Solving the Problem

The present inventors made a keen study to achieve the objects described above, and as a result, found that the deformation behavior of the rubber material can be accurately analyzed even in a micro level by using a method for predicting a deformation behavior of a rubber material, in which a three-dimensional model is generated using a binary-converted image of a rubber and a filler, each of which constitutes the rubber material; the three-dimensional model is converted into a three-layered form including a rubber portion, a filler portion and a rubber layer portion adsorbed with the filler on the basis of a molecular dynamics approach; and, a configuration condition specifying a relationship between a stress and a strain on the basis of thickness information and temperature information obtained on the basis of a molecular dynamics approach is applied to the rubber layer portion. As a result, the present inventors made the present invention.

More specifically, the method for predicting the deformation behavior of the rubber material according to the present invention includes: generating a three-dimensional model of the rubber material formed by adding a filler to a rubber; applying a configuration condition specifying a relationship between a stress and a strain on the basis of thickness information and temperature information obtained on the basis of a molecular dynamics approach to a rubber layer portion constituting the three-dimensional model; and, analyzing the deformation behavior of the rubber material.

According to a preferred example of the method for predicting a deformation behavior of a rubber material according to the present invention, the deformation behavior of the rubber material is analyzed by applying a finite element method to the three-dimensional model to which the configuration condition is applied.

Further, a device for predicting a deformation behavior of a rubber material according to the present invention includes: means for obtaining a plurality of sliced images each showing a cross-sectional shape of the rubber material formed by adding a filler to a rubber; means for converting each of the sliced images to be a binary-converted image to distinguish between a rubber portion and a filler portion contained in the rubber material; means for setting, in the binary-converted image, a rubber layer portion adsorbed with the filler, and converting the binary-converted image into a three-layered image; means for layering the three-layered image to generate a three-dimensional model of the rubber material; means for applying a configuration condition specified on the basis of a molecular dynamics approach to the three-dimensional model; means for analyzing a deformation behavior of the rubber material using the three-dimensional model to which the configuration condition is applied; and, means for presenting a result of the analysis of the deformation behavior of the rubber material.

According to a preferred example of the device for predicting a deformation behavior of a rubber material according to the present invention, the configuration condition specified on the basis of the molecular dynamics approach is a configuration condition specifying a relationship between a stress and a strain in the rubber portion, the filler portion and the rubber layer portion in accordance with three-layered values.

According to another preferred example of the device for predicting a deformation behavior of a rubber material according to the present invention, the configuration condition specified on the basis of the molecular dynamics approach is a configuration condition specifying a relationship between a stress and a strain on the basis of thickness information and temperature information of the rubber layer portion obtained on the basis of the molecular dynamics approach.

According to another preferred example of the device for predicting a deformation behavior of a rubber material according to the present invention, the means for analyzing the deformation behavior of the rubber material performs analysis by applying a finite element method to the three-dimensional model to which the configuration condition is applied.

According to the other preferred example of the device for predicting a deformation behavior of a rubber material according to the present invention, the means for presenting the result of the analysis of the deformation behavior of the rubber material calculates a strain distribution or a stress distribution on the basis of the result of the analysis; distinguishes a strain distribution area or a stress distribution area; and, specifies a position of each of the areas.

Effect of the Invention

According to the present invention, it is possible to accurately analyze a deformation behavior of a rubber material in a micro level by using a method for predicting a deformation behavior of a rubber material, in which a three-dimensional model is generated using a binary-converted image of a rubber and a filler, each of which constitutes the rubber material; the three-dimensional model is converted into a three-layered form including a rubber portion, a filler portion and a rubber layer portion adsorbed with the filler on the basis of a molecular dynamics approach; and, a configuration condition specifying a relationship between a stress and a strain on the basis of thickness information and temperature information obtained on the basis of a molecular dynamics approach is applied to the rubber layer portion. With this configuration, it is possible to predict changes of material properties due to a strain of the rubber material, and to control the material properties such as a breaking strength and loss of the rubber material.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
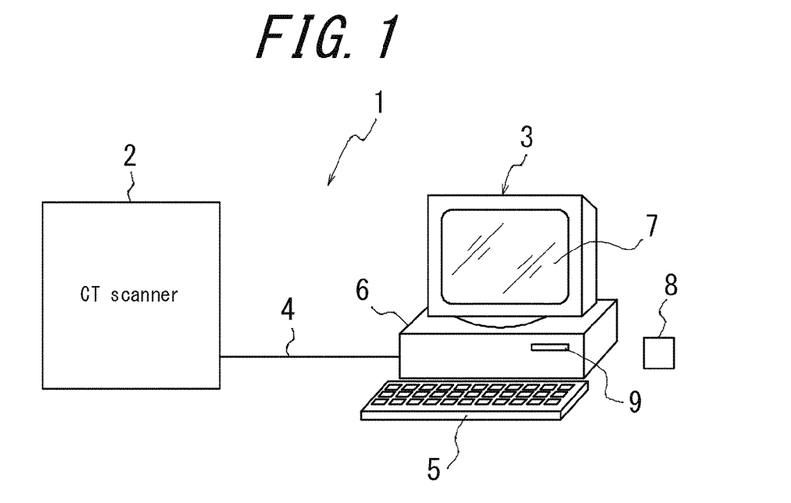
FIG. 1 is a diagram illustrating a configuration of a system for predicting a deformation behavior of a rubber material, which represents one example of a device for predicting the deformation behavior according to the present invention.
Figure 2:
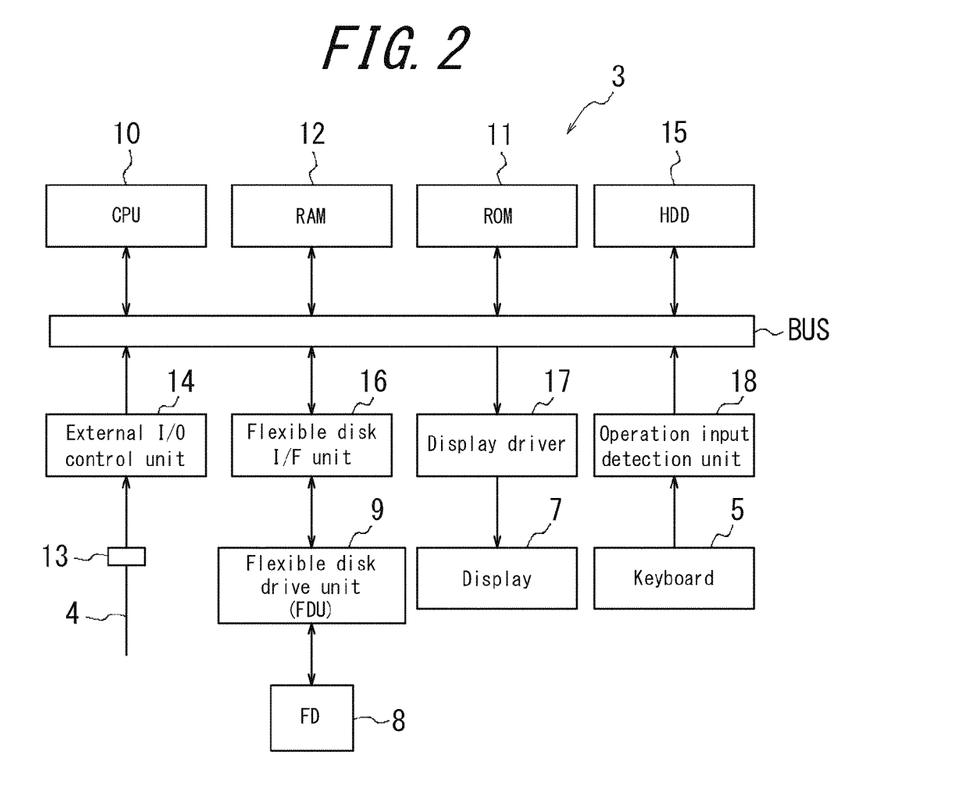
FIG. 2 is a diagram for explaining a main portion of a configuration of an electrical system of a computer constituting the system for predicting the deformation behavior of the rubber material illustrated in FIG. 1.

Hereinafter, a method for predicting a deformation behavior and a device for predicting the deformation behavior according to the present invention will be described in detail with reference to the drawings. FIG. 1 is a diagram illustrating a configuration of a system for predicting a deformation behavior of a rubber material, which serves as one example of the device for predicting the deformation behavior according to the present invention. FIG. 2 is a diagram for explaining a main portion of a configuration of an electrical system of a computer constituting the system for predicting the deformation behavior of the rubber material illustrated in FIG. 1.

A device 1 for predicting a deformation behavior illustrated in FIG. 1 includes a CT scanner (computed tomography scanner) 2, and a computer 3. The CT scanner 2 and the computer 3 are connected with each other through a cable 4.

The CT scanner 2 has a transmission electron microscope (TEM) and a sample stage. The CT scanner 2 captures an image of a rubber material that is placed on the sample stage and is to be analyzed through the transmission electron microscope, and re-structures the data obtained through the capturing to be a three-dimensional base model through a computed tomography method (CT method). Further, the CT scanner 2 slices the re-structured three-dimensional base model at predetermined intervals with respect to a predetermined plane to generate plural sliced image data. Note that, in the present invention, although not illustrated, the plural sliced images may be obtained by processing (e.g. etching) a surface of the rubber material through a focused ion beam (FIB), and observing the processed surface through a scanning electron microscope (SEM). In this case, the present invention has a scanning electron microscope system capable of emitting a focused ion beam, in lieu of the CT scanner 2.

The computer 3 has a keyboard 5 for inputting various conditions concerning analysis, a computer body 6 for analyzing the deformation behavior of the rubber material in accordance with each processing program stored in advance, and a display 7 for displaying a calculation results and the like of the computer body 6. The computer 3 analyzes the deformation behavior and the like of the rubber material using the sliced image data generated by the CT scanner 2. The computer body 6 includes a flexible disk drive unit (hereinafter, referred to as FDU) 9 into/from which a flexible disk (hereinafter, referred to as FD) 8 serving as a recording medium can be inserted/removed.

As illustrated in FIG. 2, the computer 3 includes a central processing unit (CPU) 10 for governing operations of the device as a whole; a ROM 11 for storing, in advance, various programs including a controlling program for controlling the computer 3, various parameters and the like; a RAM 12 for temporarily storing various kinds of data; an external I/O control unit 14 connected with a connector 13 connected with the cable 4 for obtaining the sliced image data from the CT scanner 2 through the connector 13; a hard disk drive (HDD) 15 for storing the obtained sliced image data; a flexible disk I/F unit 16 for inputting/outputting data with the FD 8 provided to the FDU 9; a display driver 17 for controlling displaying of various types of information on the display 7; and, an operation input detection unit 18 for detecting a key operation to the keyboard 5.

The CPU 10, the RAM 12, the ROM 11, the HDD 15, the external I/O control unit 14, the flexible disk I/F unit 16, the display driver 17, and the operation input detection unit 18 are connected with each other through a system bus BUS. With this configuration, the CPU 10 can access the RAM 12, the ROM 11 and the HDD 15; access the FD 8 provided to the FDU 9 through the flexible disk I/F unit 16; control transmission/reception of data through the external I/O control unit 14; and, display various types of information on the display 7 through the display driver 17. Further, the CPU 10 can know the key operation to the keyboard 5 at all times.

It should be noted that it is possible to read/write the processing programs, data and the like from/to the FD 8 using the FDU 9. Therefore, it may be possible to record the processing programs, data and the like in the FD 8 in advance, and execute the processing programs recorded in the FD 8 through the FDU 9. Further, it may be possible to install, to the HDD 15, the processing programs recorded in the FD 8 and execute the installed processing programs. Yet further, as the recording medium, it may be possible to employ a recording tape, an optical disk such as a CD-ROM and DVD, and a magneto-optical disk such as a MD and MO. In the case of employing these recording media, a read/write unit is used in place of the FDU 9, or a read/write unit compatible with the FDU 9 is used.

Further, the configuration of the system for predicting the deformation behavior of the rubber material illustrated in FIG. 1 is merely an example, and depending on applications, it may be possible to modify a known configuration as needed.

Figure 2A:
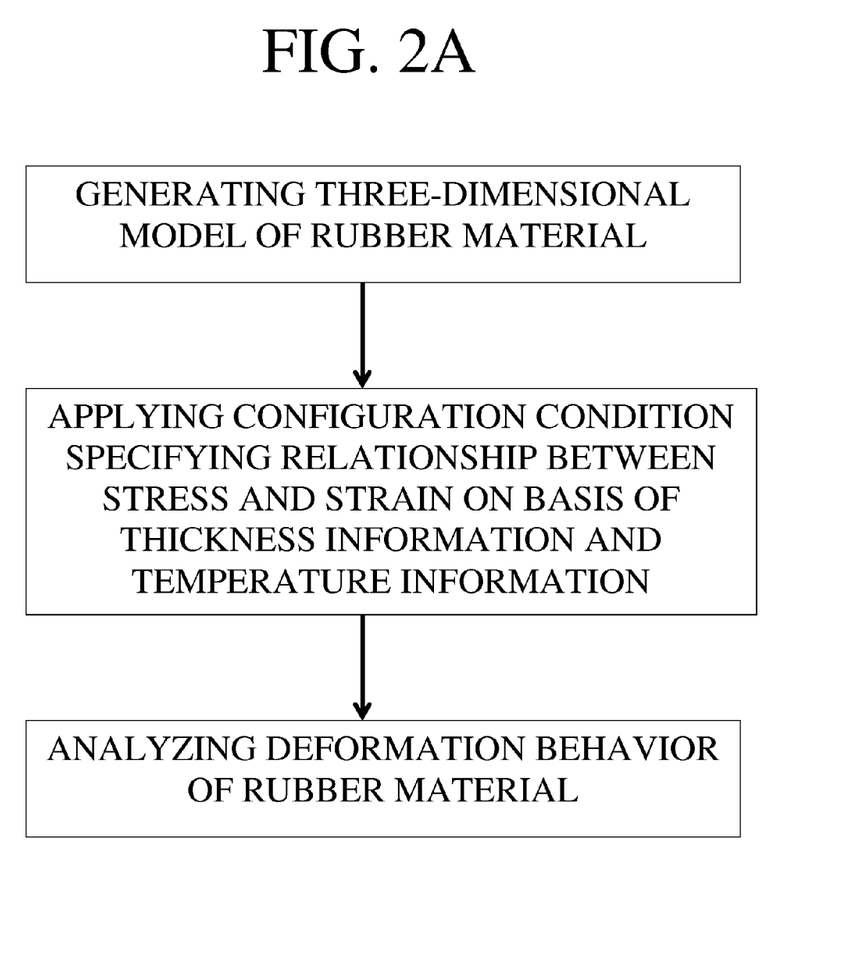
FIG. 2A is a flow chart illustrating a method of predicting a deformation behavior of a rubber material.

Hereinbelow, a method for predicting a deformation behavior of a rubber material according to the present invention will be described in detail as illustrated in FIG. 2A. The method for predicting the deformation behavior of the rubber material according to the present invention provides a method for predicting a deformation behavior of a rubber material, which obtains plural sliced images each showing a cross-sectional shape of the rubber material formed by adding a filler to a rubber; converts each of the sliced images to be a binary-converted image to distinguish between the rubber portion and the filler portion contained in the rubber material, thereby generating a three-dimensional model; and, in this method for predicting the deformation behavior, the three-dimensional model is formed into a three-layered form having the rubber portion, the filler portion and a rubber layer portion adsorbed with the filler on the basis of a molecular dynamics approach, and a configuration condition specifying a relationship between a stress and a strain on the basis of thickness information and temperature information obtained from the molecular dynamics approach is applied to the rubber layer portion. By applying, to the rubber layer portion, the specific configuration condition obtained from the molecular dynamics approach, it is possible to take the rubber layer portion into consideration at the time of predicting the deformation behavior of the rubber material, whereby it is possible accurately analyzing the deformation behavior of the rubber material.

In the method for predicting the deformation behavior according to the present invention, plural sliced images each showing a cross-sectional shape of the rubber material formed by adding the filler to the rubber are first obtained to understand an internal structure of the rubber material. In the system for predicting the deformation behavior of the rubber material illustrated in FIG. 1, a user applies a marking with a gold colloid to the rubber material to be analyzed, and places the rubber material on the sample stage provided to the CT scanner 2. Then, an operation for starting the process is performed to the CT scanner 2 to capture the sliced images. Note that the CT scanner 2 is configured by a measurement device having a computer configuration using the transmission electron microtomography method (TEMT). The CT scanner 2 scans while rotating and moving the transmission electron microscopy and the sample stage, on which the rubber material is placed, relatively to each other for each predetermined angle (for example, at each 2 degree) within a predetermined angle range (for example, in the range of −60 degrees to +60 degrees) to capture the continuous angled images of the rubber material. The CT scanner 2 obtains a rotation axis between the images, by using image data of the captured plural angled images (for example, 61 images), and re-structures them to be three-dimensional base model through the computed tomography method. Then, the CT scanner 2 generates sliced images, which are obtained by slicing the re-structured three-dimensional base model at predetermined intervals (for example, 4 nm intervals) at planes parallel to the respective planes of the three-dimensional base model.

It should be noted that the rubber material is obtained by adding the filler to the rubber, and, depending on applications, it may be possible to select the rubber and the filler described above from those ordinary used in the field of the rubber industry. Further, the shape of the rubber material is not specifically limited, but it is preferable that the rubber material is formed in a shape from which sliced images can be easily obtained with the CT scanner 2, and more specifically, is formed in a hexahedral shape such as a cube and rectangular parallelepiped.

Next, in the method for predicting the deformation behavior according to the present invention, the plural sliced images each showing the cross-sectional shape of the rubber material obtained through the processes above are converted into binary images to determine the rubber portion and the filler portion contained in the rubber material. In the sliced images described above, since transmissivity is materially different between the rubber portion and the filler portion, each of which constitutes the rubber material, the filler portion is dark (having large density value) and the rubber portion is light (having small density value) in general. Therefore, it is possible to determine the rubber portion and the filler portion in the sliced images on the basis of the degree of denseness of each pixel in the sliced images. The density value for determining the rubber portion and the filler portion in the sliced images can be specified in advance through experiments and the like.

Figure 3:
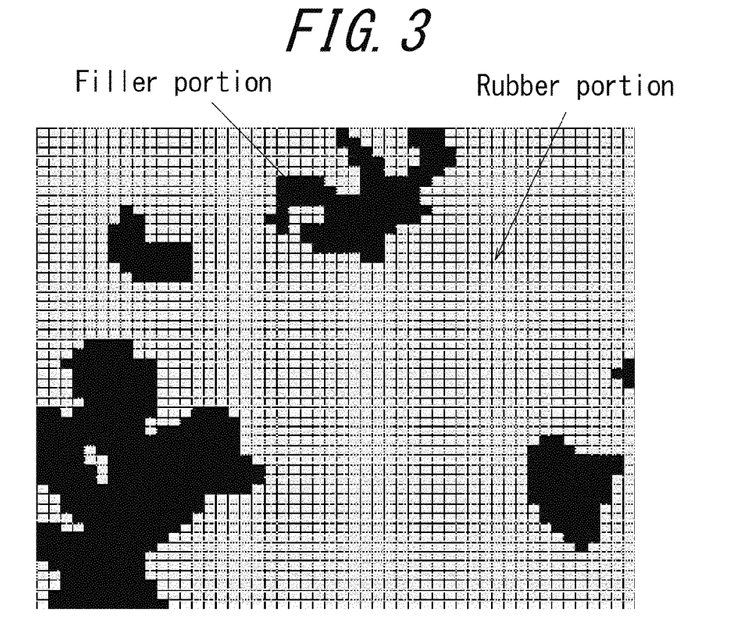
FIG. 3 is a diagram illustrating a binary-converted image obtained by converting a sliced image into a binary form.

In the system for predicting the deformation behavior of the rubber material illustrated in FIG. 1, the density value specified in advance through experiments and the like and used for determining the rubber portion and the filler portion in the sliced images is set as a threshold value h; density values of pixels in the sliced images are each compared with the threshold value h; each of the pixels is converted into a binary number to obtain binary-converted images, thereby generating binary-converted image data. FIG. 3 is a diagram illustrating a binary-converted image obtained by converting the sliced image into a binary form.

It should be noted that, to further precisely extract the filler portion in the rubber material, the process of converting into the binary image includes: comparing the density value of each of the pixels in the sliced images with the threshold value h; and, blackening a pixel located at a portion where the predetermined number (for example, five or more) of pixels having a density value more than or equal to the threshold value h are disposed continuously in a vertical direction and a horizontal direction and whitening the other pixels to obtain binary-converted images, thereby generating the binary-converted image data. Further, it may be possible to convert a format of the colored binary-converted image data into a binary-converted image data in which a value of each of the pixels in the blackened portion is "1" and a value of each of the pixels in the whitened portion is "0."

Figure 4:
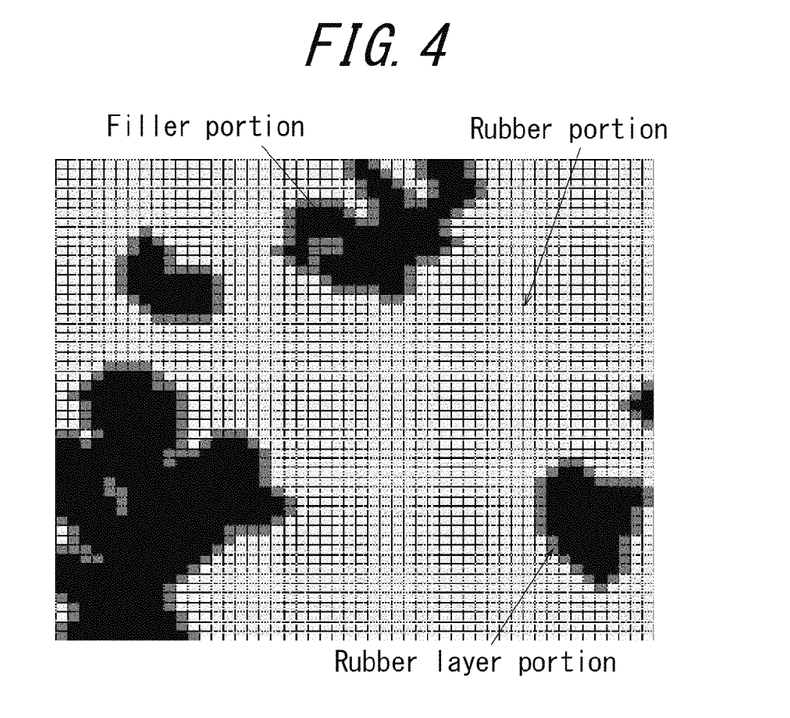
FIG. 4 is a diagram illustrating a three-layered image obtained by converting the binary-converted image into a ternary form.

In the method for predicting the deformation behavior according to the present invention, by specifying the rubber layer portion adsorbed with the filler, the binary-converted image is converted into a three-layered image. As described later, with the conversion into the three-layered image, the three-dimensional model of the rubber material can be converted into the three-layered model on the basis of the molecular dynamics approach. In the system for predicting the deformation behavior of the rubber material illustrated in FIG. 1, the binary-converted image data whose format has been converted as described above is further format-converted into the three-layered image, by converting such that a value of a pixel that has a value of "0" and whose next pixel has a value of "1" is changed to be "2." More specifically, the value of the pixel of the rubber layer portion adsorbed with the filler is "2." FIG. 4 is a diagram illustrating the three-layered image obtained by converting the binary-converted image into a ternary-converted image, in which the filler portion, the rubber portion and the rubber layer portion adsorbed with the filler are black, white and gray, respectively. It should be noted that the method for determining the rubber layer portion as described above is merely one example, and it may be possible to determine the rubber layer portion according to the size of the pixel depending on applications. For example, it is possible to further precisely analyze the deformation behavior, by setting the other rubber portion as the rubber layer portion, rather than limiting the rubber layer portion to pixels of the rubber portion adjacent to the pixels of the filler portion, so that the rubber layer portion has a certain thickness, or by converting the rubber layer portion into further multiple parts.

Next, in the method for predicting the deformation behavior according to the present invention, three-layered images are layered to generate a three-dimensional model of the rubber material. In the system for predicting the deformation behavior of the rubber material illustrated in FIG. 1, the format-converted three-layered images are layered in a manner that meets condition such as a position at which corresponding sliced images are obtained, and a three-dimensional structure of the rubber material is formed, whereby it is possible to generate a three-dimensional model in which each pixel in the three-layered images is set to a unit of cell. More specifically, in the format-converted three-layered image of the three-dimensional model as described above, a portion with a pixel value of "0" represents the rubber portion; a portion with a pixel value of "1" represents the filler portion; and, a portion with a pixel value of "2" represents the rubber layer portion adsorbed with the filler. Note that, as for the generated three-dimensional model of the rubber material, it may be possible to generate a computational stereoscopic image of the rubber material to produce the stereoscopic image on the display 7, by performing image processing capable of integrating three-layered images by placing pixels having the same value in the same cell area between the three-layered images.

In the method for predicting the deformation behavior according to the present invention, since the three-dimensional model described above are formed in three layers including the rubber portion, the filler portion and the rubber layer portion adsorbed with the filler on the basis of the molecular dynamics approach, it is necessary to apply configuration condition specified on the basis of the molecular dynamics approach to the three-dimensional model generated by layering the three-layered images. More specifically, the configuration condition is specified on the basis of the molecular dynamics approach such that configuration condition different from that applied to the rubber portion is applied to the rubber layer portion adsorbed with the filler.

Figure 5:
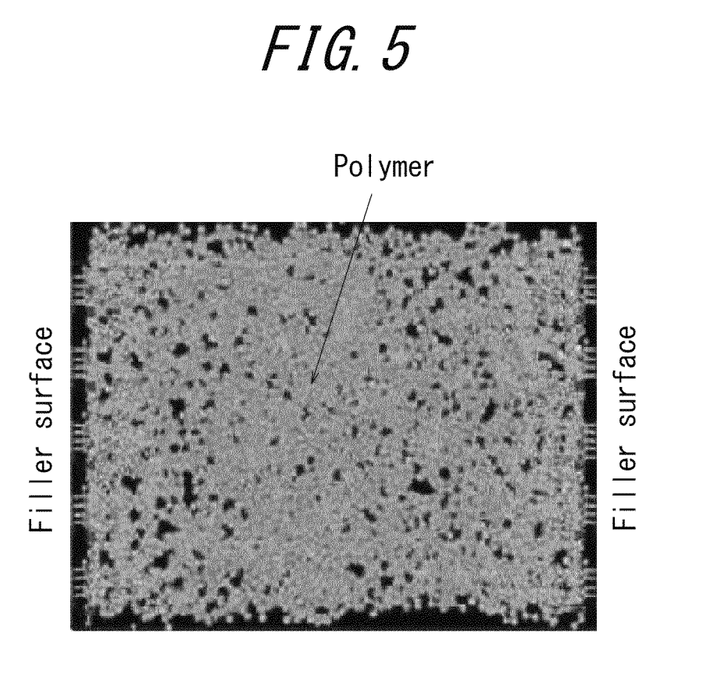
FIG. 5 is a schematic view illustrating a system formed by a filler and a polymer obtained on the basis of a molecular dynamics approach.
Figure 6:
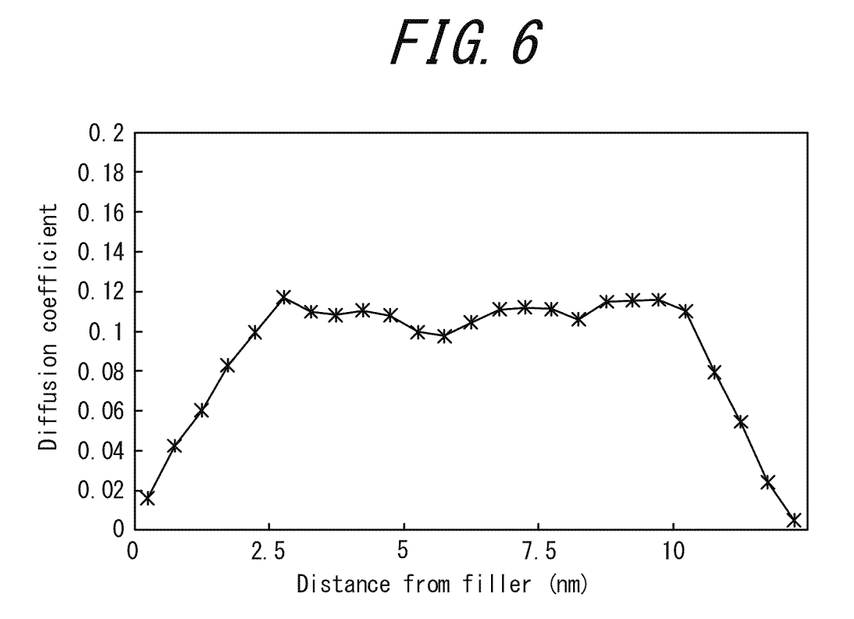
FIG. 6 is a diagram illustrating a relationship between the distance from a filler surface and a diffusion coefficient.
Figure 7:
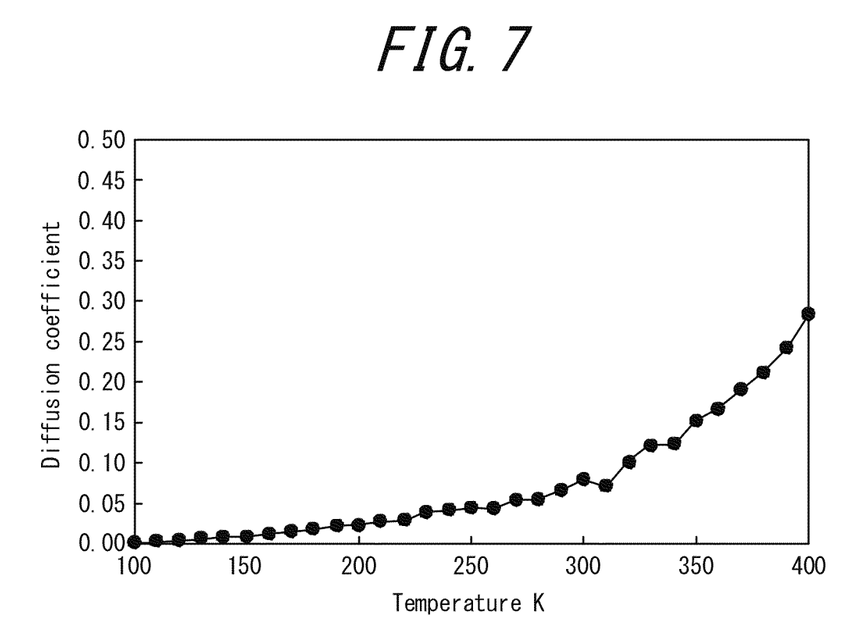
FIG. 7 is a diagram illustrating a relationship between a diffusion coefficient of the rubber and temperature.

Below, description will be made of one example of a method of determining the configuration condition applied to the rubber layer portion adsorbed with the filler of the rubber material. First, a system formed by filler surfaces and a rubber (polymer) is structured on the basis of the molecular dynamics approach. FIG. 5 is a schematic view illustrating the system formed by the filler and the polymer obtained on the basis of the molecular dynamics approach. Then, mean square displacement of the rubber in the system is calculated to obtain diffusion coefficient on the basis of the result of the calculation. FIG. 6 is a diagram illustrating a relationship between the distance from the filler surface and the diffusion coefficient, in which the y axis represents the diffusion coefficient and the x axis represents the distance from the filler surface. Note that: the x axis corresponds to FIG. 5; both ends of the x axis represent positions of the respective filler surfaces; and, scales on the x axis each represent the distance from the filler surface on one side. From FIG. 6, it can be understood that the rubber layer portion adsorbed with the filler has a smaller diffusion coefficient as compared with the rubber portion due to bond of the filler. Further, in parallel with the calculation, a rate of change of mean square displacement of the polymer itself with respect to temperature is calculated to obtain the temperature dependence of the diffusion coefficient of the polymer. FIG. 7 is a diagram illustrating a relationship between the diffusion coefficient of the rubber and temperature, in which the y axis represents the diffusion coefficient and the x axis represents temperatures. From FIG. 7, it can be understood that the diffusion coefficient of the rubber increases with the increase of temperature, and in particular, sharply increases from the vicinity of the glass transition point (around −52° C.). More specifically, this means that, in the rubber layer portion having the smaller diffusion coefficient, the rubber is in the low temperature state. This fact supports the general idea that the polymer phase existing in the vicinity of the filler is in the vitreous state. As can be clearly understood from the results, by changing configuration conditions from those conventionally applied to the rubber portion in which temperature is not changed, into those in which temperature varies, it is possible to input the change of material properties according to distances from the filler, whereby it is possible to precisely analyze the actual deformation behavior of the rubber material in a micro level.

It should be noted that it is preferable to apply the configuration condition specifying a relationship between a stress and a strain to the rubber layer portion of the three-dimensional model, and it is further preferable to, as described above, apply the configuration condition specifying a relationship between a stress and a strain on the basis of thickness information and temperature information obtained on the basis of the molecular dynamics approach. More specifically, the relationship between the stress and the strain actually measured at temperatures corresponding to the diffusion coefficient at the rubber layer portion is applied, as the configuration condition, to the cell area corresponding to the rubber layer portion of the three-dimensional model. Note that the configuration conditions specifying the relationship between the stress and the strain include a generalized Mooney-Rivlin equation and a generalized Ogden equation as described in Japanese Patent Application Laid-open No. 2006-200937, and the following equation (1) disclosed in Japanese Patent Application Laid-open No. 2005-345413:

$$G = P \cdot \frac{\exp(\beta \cdot k) \cdot \cosh(2\beta \cdot I_1) - 1}{\exp(\beta \cdot k) \cdot \cosh(2\beta \cdot I_1) + 1} + Q \cdot \frac{T}{\Delta T} \cdot \frac{\partial S}{\partial I_1} \quad (1)$$

[where G represents Young's modulus; S represents entropy change at the time of rubber deformation; P and Q each represent a coefficient related to an elastic modulus; $I_1$ represents an invariant of strain; T represents absolute temperatures; $\beta$ is equal to $1/(k\Delta T)$; k represents a Boltzmann constant; and, $\Delta T$ represents a difference from a glass transition temperature of the rubber].

In the case where the configuration conditions specifying the relationship between the stress and the strain of the filler are obtained in advance as the configuration conditions of the filler portion in the three-dimensional model, it is preferable to apply these configuration conditions to the cell area of the filler portion in the three-dimensional model. Alternatively, it may be possible to use, as the configuration conditions, an actual value obtained by measuring the hardness of the filler in advance through an experiment, or an estimated value obtained from a ratio between a crystal portion and an amorphous portion in the filler. Further, in general, the filler contained in the rubber material is harder than the rubber and has a larger Young's modulus (elastic modulus) than that of the rubber, whereby it may be possible to apply, as the configuration conditions for the filler portion in the three-dimensional model, a Young's modulus predetermined times (for example, 1000 times) larger than the Young's modulus obtained from the configuration conditions applied to the rubber portion.

Further, it is preferable to apply the configuration conditions specifying the relationship between the stress and the strain to the rubber portion of the three-dimensional model, and it is possible to preferably use the generalized Mooney-Rivlin equation and a generalized Ogden equation as described in Japanese Patent Application Laid-open No. 2006-200937, the equation (1) described above and the like.

Next, in the method for predicting the deformation behavior according to the present invention, the deformation behavior of the rubber material is analyzed using the three-dimensional model to which the configuration conditions described above are applied. In the system for predicting the deformation behavior of the rubber material illustrated in FIG. 1, a three-dimensional model to be analyzed and a condition for the analysis are input through the keyboard 15 by the user, and are provided to the computer 12, and then, a process of analyzing the deformation behavior of the rubber material is performed. Note that, as the conditions for the analysis, it is possible to specify a direction to which the three-dimensional model is changed, and a rate of change at the time when the three-dimensional model is subjected to stretch, compressive or shearing deformation in the specified direction. Further, through the process of the analysis, it is possible to analyze a strain and a distribution of internal stress in the three-dimensional model, and a stress value of the entire three-dimensional model at the time when the three-dimensional model is subjected to the stretch, compressive or shearing deformation in the direction specified as the condition for the analysis, and display the results of the analysis on the display 7. Since the three-dimensional model to which the configuration condition described above is applied has a structure similar to that of the actual rubber material, it is possible to precisely analyze the elastic modulus and the stress distribution in the rubber material, by analyzing the deformation behavior of the rubber material using the finite element method (FEM).

Below, a detailed description will be made of a device for predicting the deformation behavior of the rubber material according to the present invention. The device for predicting the deformation behavior of the rubber material according to the present invention relates to a device for performing the method for predicting the deformation behavior described above, and includes the system for predicting the deformation behavior of the rubber material illustrated in FIG. 1. More specifically, the device for predicting the deformation behavior according to the present invention includes means for obtaining plural sliced images each showing a cross-sectional shape of the rubber material formed by adding the filler to the rubber; means for converting each of the sliced images to be a binary-converted image to distinguish between the rubber portion and the filler portion contained in the rubber material; means for setting, in the binary-converted image, a rubber layer portion adsorbed with the filler to convert the binary-converted image into the three-layered image; means for layering the three-layered image to generate a three-dimensional model of the rubber material; means for applying a configuration condition specified on the basis of a molecular dynamics approach to the three-dimensional model; means for analyzing a deformation behavior of the rubber material using the three-dimensional model to which the configuration condition is applied; and, means for presenting a result of the analysis of the deformation behavior of the rubber material.

In the means for applying the configuration condition specified on the basis of the molecular dynamics approach to the three-dimensional model in the device for predicting the deformation behavior according to the present invention, it is preferable that the configuration condition specified on the basis of the molecular dynamics approach is a configuration condition specifying a relationship between the stress and the strain in the rubber portion, the filler portion and the rubber layer portion in accordance with three-layered values, and is a configuration condition specifying a relationship between the stress and the strain on the basis of the thickness information and the temperature information of the rubber layered portion obtained on the basis of the molecular dynamics approach.

In the device for predicting the deformation behavior according to the present invention, it is preferable that the means for analyzing the deformation behavior of the rubber material performs its analysis by applying the finite element method to the three-dimensional model to which the configuration condition described above is applied. Further, it is preferable that the means for presenting a result of the analysis of the deformation behavior of the rubber material calculates a strain distribution or a stress distribution on the basis of the result of the analysis; distinguishes a strain distribution area or a stress distribution area; and, specifies positions of each of the areas.

EXAMPLE

Below, the present invention will be described more in detailed by giving an example. However, the present invention is not limited to the following example.

In the system for predicting the deformation behavior of the rubber material illustrated in FIG. 1, a rubber material formed by adding 30 mass parts of carbon black to 100 mass parts of rubber is captured with a three-dimensional transmission electron microscopy to generate a three-dimensional model of the rubber material. As the thus obtained three-dimensional model is formed into three layers, the constitutive equation expressed by the equation (1) described above and representing a temperature dependence and a strain dependence of an elastic modulus, and a Young's modulus (elastic modulus) obtained on the basis of the actually measured value or estimated value described above are applied, as configuration conditions, to cell areas of the rubber portion and the filler portion, and, configuration conditions specifying a relationship between a stress and a strain on the basis of thickness information and temperature information obtained on the basis of the molecular dynamics approach are applied to a cell area of the rubber layer portion. Further, an FEM calculation is performed to the three-dimensional model to which the configuration conditions are applied. The results thereof are shown in FIG. 8 through FIG. 11.

Figure 8:
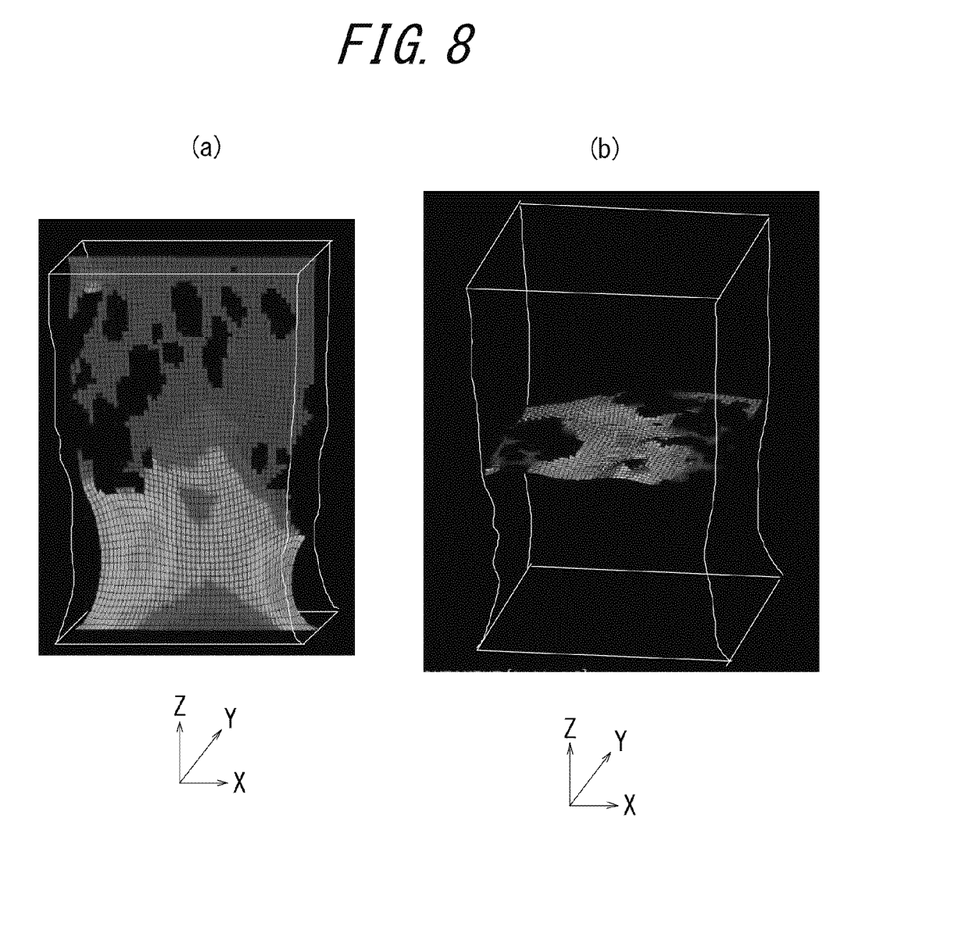
FIG. 8 is a sectional image view illustrating results of analysis of a deformation behavior of a rubber material.

FIG. 8 is a sectional image view illustrating results of the analysis of the deformation behavior of the rubber material. Note that FIG. 8 shows the results of the analysis of the strain state and the stress distribution in the case where the entire three-dimensional model is stretched by 15% in the z direction using the three-dimensional model data. As for the stress distribution, the denser portion indicates the higher stress value.

Figure 9:
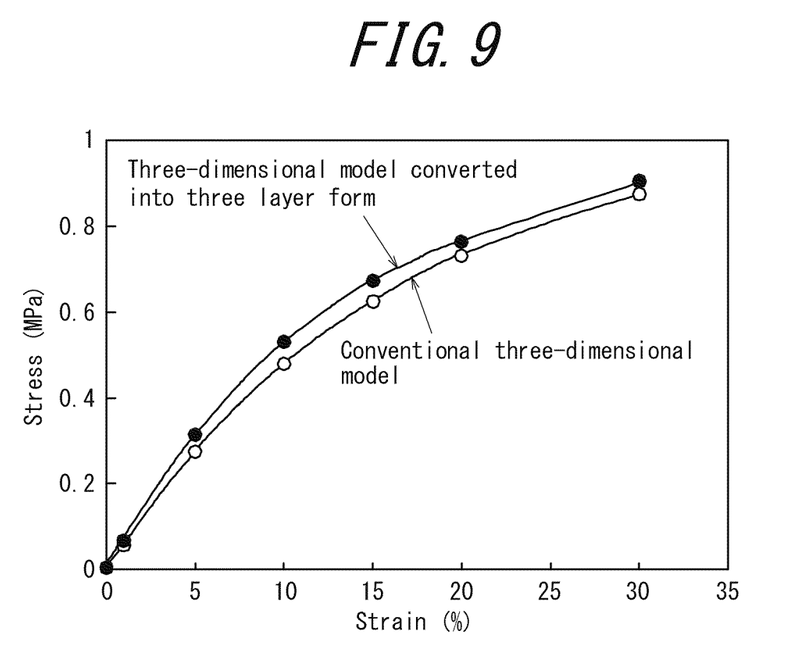
FIG. 9 is a diagram illustrating a stress-strain curve of the rubber material obtained from an FEM calculation.
Figure 10:
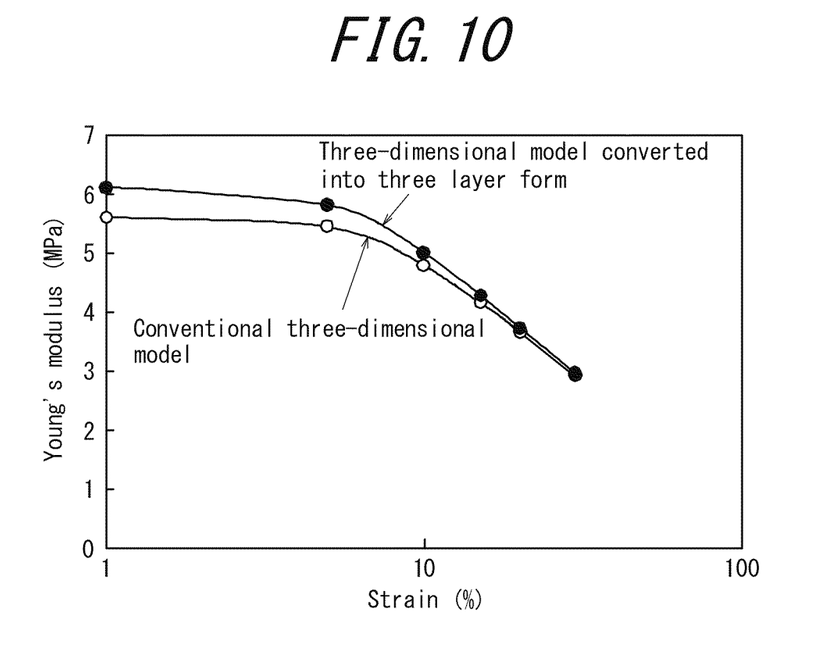
FIG. 10 is a diagram obtained by converting the relationship illustrated in FIG. 9 into a relationship between a Young's modulus and a strain.

FIG. 9 is a diagram illustrating a stress-strain curve of the rubber material obtained from the FEM calculation, and FIG. 10 is a diagram obtained by converting the relationship illustrated in FIG. 9 into a relationship between the Young's modulus and the strain. From these results, it can be known that the three-layered three-dimensional model shows a deformation behavior different from the conventional three-dimensional model in which the rubber portion and the filler portion are binary converted.

The above-described results represent the deformation behavior of the rubber material in a micro level with an extremely high accuracy. Therefore, on the basis of the results of analysis described above, it is possible to precisely predict the deformation behavior of the actual rubber material, whereby it is possible to effectively control the material properties such as a breaking strength and loss of the rubber material.

EXPLANATION OF REFERENCE NUMERALS

1 System for predicting deformation behavior of rubber material
3 Computer
4 Cable
5 Keyboard
6 Computer body
7 Display
8 FD
9 FDU
13 Connector

The invention claimed is:

1. A method for predicting a deformation behavior of a rubber material, including:
    generating a three-dimensional model of the rubber material formed by adding a filler to a rubber;
    applying a configuration condition specifying a relationship between a stress and a strain on the basis of thickness information and temperature information obtained on the basis of a molecular dynamics approach to a rubber layer portion constituting the three-dimensional model; and,
    analyzing the deformation behavior of the rubber material, wherein the deformation behavior of the rubber material is analyzed by applying a finite element method to the three-dimensional model to which the configuration condition is applied,
    wherein the thickness information comprises information including a relationship between a distance from a filler surface and a diffusion coefficient of the rubber material, and
    wherein the temperature information comprises information including a relationship between a temperature and a diffusion coefficient of the rubber material.

2. A device for predicting a deformation behavior of a rubber material, comprising:
    means for obtaining a plurality of sliced images each showing a cross-sectional shape of the rubber material formed by adding a filler to a rubber;
    means for converting each of the sliced images to be a binary-converted image to distinguish between a rubber portion and a filler portion contained in the rubber material;

means for setting, in the binary-converted image, a rubber layer portion adsorbed with the filler, and converting the binary-converted image into a three-layered image;

means for layering the three-layered image to generate a three-dimensional model of the rubber material;

means for applying a configuration condition specified on the basis of a molecular dynamics approach to the three-dimensional model;

means for analyzing a deformation behavior of the rubber material using the three-dimensional model to which the configuration condition is applied, wherein the means for analyzing the deformation behavior of the rubber material performs analysis by applying a finite element method to the three-dimensional model to which the configuration condition is applied; and, means for presenting a result of the analysis of the deformation behavior of the rubber material, wherein the configuration condition specified on the basis of the molecular dynamics approach is a configuration condition specifying a relationship between a stress and a strain on the basis of thickness information and temperature information of the rubber layer portion obtained on the basis of the molecular dynamics approach, wherein the thickness information comprises information including a relationship between a distance from a filler surface and a diffusion coefficient of the rubber material, and wherein the temperature information comprises information including a relationship between a temperature and a diffusion coefficient of the rubber material.

3. The device for predicting a deformation behavior of a rubber material according to claim 2, wherein the configuration condition specified on the basis of the molecular dynamics approach is a configuration condition specifying a relationship between a stress and a strain in the rubber portion, the filler portion and the rubber layer portion in accordance with three-layered values.

4. The device for predicting a deformation behavior of a rubber material according to claim 2, wherein the means for presenting the result of the analysis of the deformation behavior of the rubber material calculates a strain distribution or a stress distribution on the basis of the result of the analysis; distinguishes a strain distribution area or a stress distribution area; and, specifies a position of each of the areas.

* * * * *